United States Patent [19]
Gisin et al.

[11] Patent Number: 5,507,801
[45] Date of Patent: Apr. 16, 1996

[54] COMPRESSION DRILL GUIDE

[75] Inventors: Paul Gisin, Waldenburg; Stephan M. Perren, Davos-Dorf, both of Switzerland

[73] Assignee: Synthes (U.S.A.), Paoli, Pa.

[21] Appl. No.: 991,515

[22] Filed: Dec. 16, 1992

Related U.S. Application Data

[63] Continuation of Ser. No. 710,408, Jun. 5, 1991, abandoned.

[30] Foreign Application Priority Data

Jun. 6, 1990 [CH] Switzerland ............ 01903/90

[51] Int. Cl.⁶ .................. A61F 5/00; A61B 17/58
[52] U.S. Cl. .................... 606/86; 606/96
[58] Field of Search .............. 606/96, 97, 98, 606/86, 87, 88, 63, 69, 70, 71; 408/72 R, 81, 112

[56] References Cited

U.S. PATENT DOCUMENTS

| | | | |
|---|---|---|---|
| 2,224,480 | 12/1940 | Kartarik. | |
| 2,421,354 | 5/1947 | Reiter | 606/100 |
| 2,725,878 | 12/1955 | Reiter | 606/100 |
| 2,985,168 | 5/1961 | Jonas | 606/96 |
| 3,036,482 | 5/1962 | Kenworthy | 606/100 |
| 3,540,322 | 11/1970 | Swanson | 408/112 |
| 3,986,504 | 10/1976 | Avila | 606/63 |
| 4,341,206 | 7/1982 | Perrett | 606/97 |
| 4,493,317 | 1/1985 | Klaue | 606/96 |
| 4,535,768 | 8/1985 | Hourahane | 606/86 |
| 4,549,538 | 10/1985 | Schadrack | 606/96 |
| 4,570,624 | 2/1986 | Wu | 606/96 |
| 4,599,999 | 7/1986 | Klaue | 606/96 |
| 5,047,034 | 9/1991 | Sohngen | 606/87 |
| 5,112,335 | 5/1992 | Laboureau | 606/96 |

FOREIGN PATENT DOCUMENTS

| | | | |
|---|---|---|---|
| 3312250 | 10/1984 | Germany. | |
| 1225544 | 4/1986 | U.S.S.R. | 606/86 |
| 1584916 | 8/1990 | U.S.S.R. | 606/96 |

Primary Examiner—Michael A. Brown
Attorney, Agent, or Firm—Fish & Richardson

[57] ABSTRACT

A drill guide for drilling screw holes in bone fragments that are to be stabilized by means of a device composed of a compression plate and round-headed screws, the drill guide having a hollow outer cylinder and hollow inner cylinder, positioned so that the hollow inner cylinder can be slid axially within the outer cylinder by means of a spring mechanism, the plate-side end of the outer cylinder and the plateside of the inner cylinder having the shape of the spherical underside of the head and the shank of the screws to be used, respectively.

5 Claims, 6 Drawing Sheets

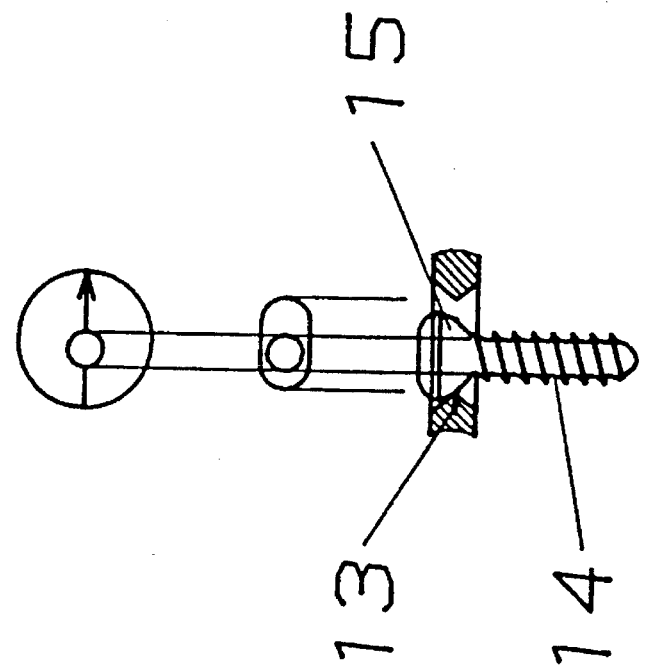
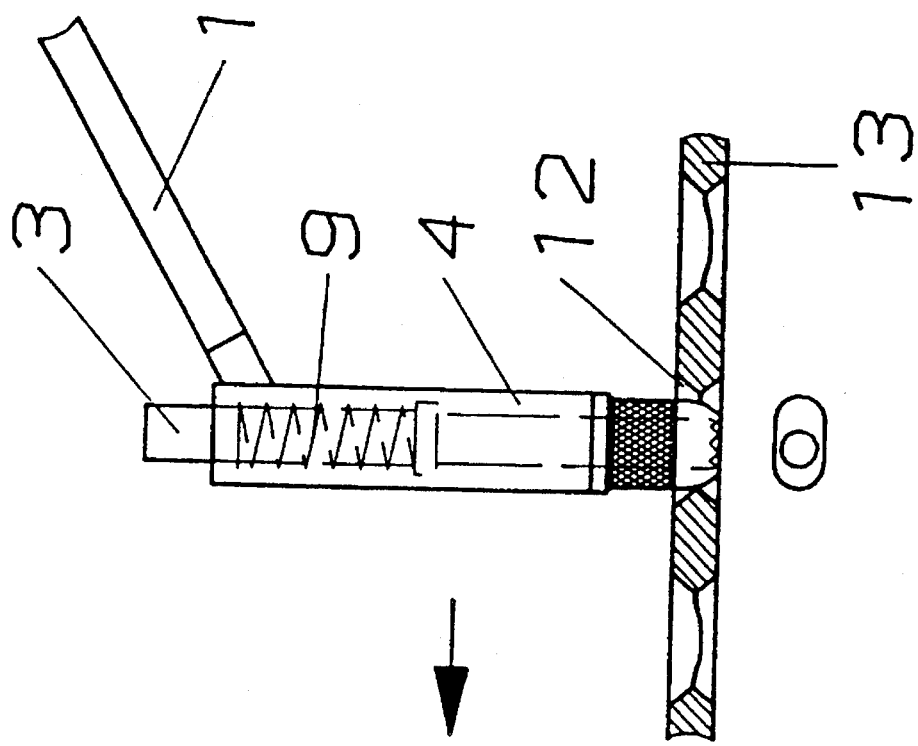

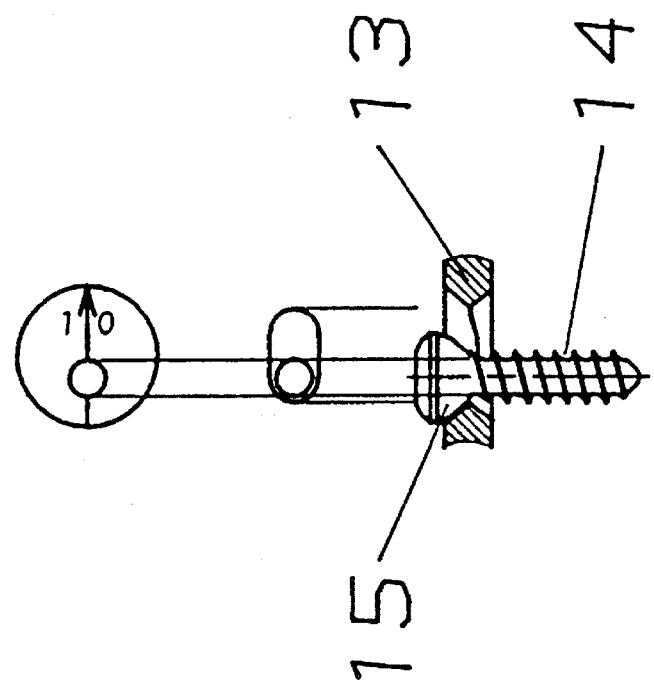
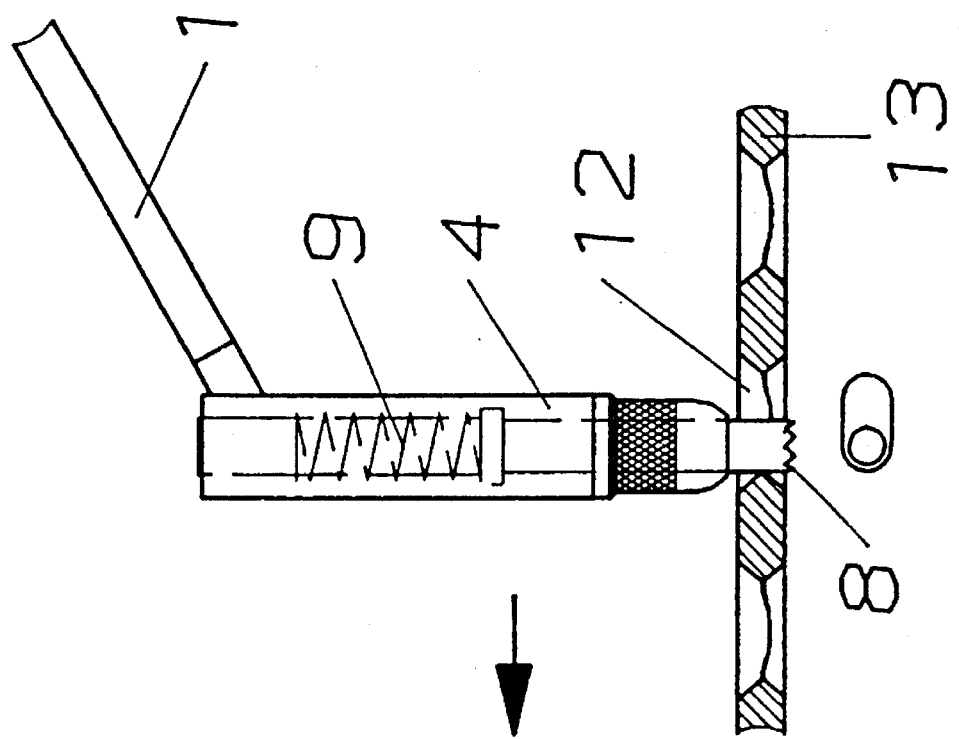

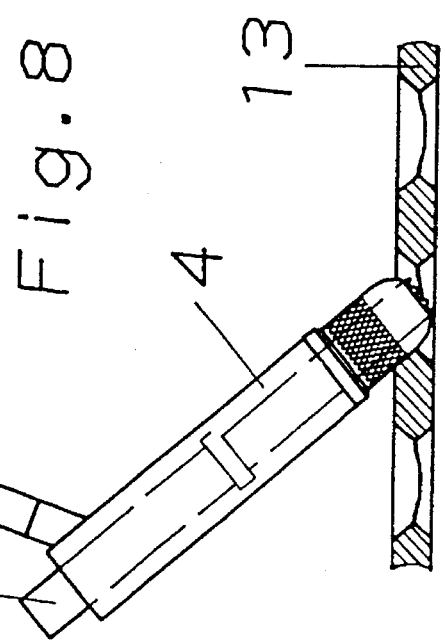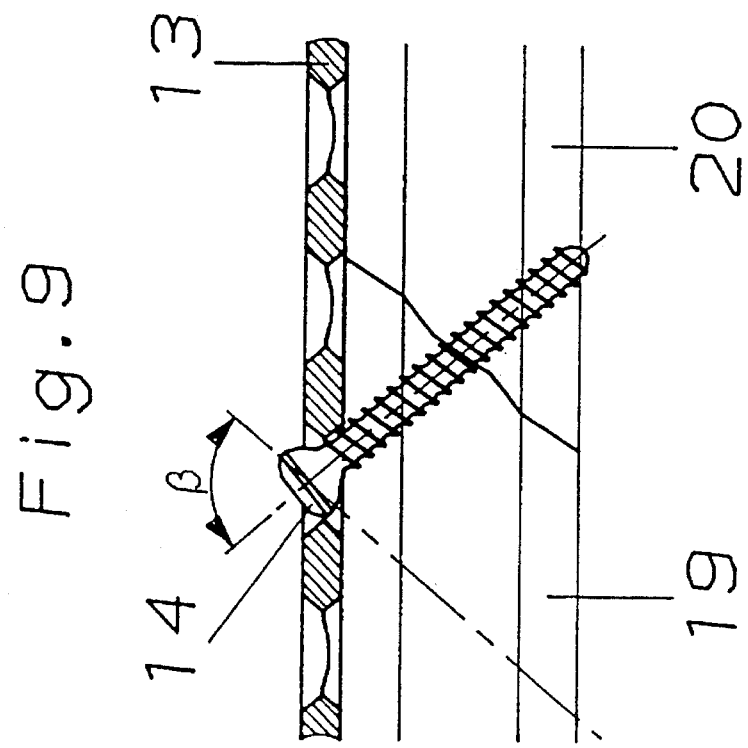

COMPRESSION DRILL GUIDE

This is a continuation of application Ser. No. 07/710,408 filed on Jun. 5, 1991, now abandoned.

FIELD OF THE INVENTION

This invention relates to a drill guide for drilling holes in bone fragments to be stabilized by means of compression bone plates fixed to the bone by screws, and in particular, to a drill guide suitable for use where the screws are to be positioned neutrally rather than eccentrically with respect to the screw holes in the plate; or obliquely angled with respect to the plane of the plate.

BACKGROUND

A drill guide for use in compression osteosynthesis is disclosed in EP-B1 O 173 267. In this drill guide the actual drill bushing is positioned eccentrically, so that a pre-determined compression effect can be achieved.

A disadvantage of this drill guide is that it pays insufficient attention to the geometry of the shank of the screw to be inserted. The plate end of this known guide merely simulates the geometry of the head of the screw to be inserted. This can be inadequate when the hole to be bored is oblique to the plane of the compression plate. Another disadvantage is that the known drill guide permits the execution of eccentric bores only, and thus makes it necessary to use another guide for neutral screw positionings. With conventional drill guides it is not possible to achieve a spherical seating in the screw hole, so there is no guaranty of a stress-free osteosynthesis, that is, one that is free from parasitic additional loads.

SUMMARY OF THE INVENTION

The invention provides a drill guide for use in osteosynthesis which can be used to drill holes positioned neutrally, as well as offset, in a wide range of angles to the surface of the bone or the plane of the compression plate to be applied.

More specifically, the invention provides a drill guide for drilling holes in segments of fractured bones to be stabilized by means of a compression bone plate having screw holes and round headed screws adapted to fit said screw holes, the guide comprising a hollow outer cylinder, a hollow inner cylinder slidingly positioned in said outer cylinder, and a spring mechanism in said outer cylinder acting upon said inner cylinder to extend the distal (or plate) end of the inner cylinder beyond the distal end of the outer cylinder. The shape of the distal end of the outer cylinder will be identical to that of the head of the screw to be employed. The distal or plate end of the inner cylinder will have the shape and diameter of the shank of the screw to be employed.

Among the advantages achieved through the invention is that thanks to the fact that the exterior shape of the distal segment is completely identical to the exterior contour of the bone screw to be used, even during drilling preparations the position of the screw head—relative to the drill hole—can be selected with the greatest precision. By means of a drill guide according to the invention, both the longitudinal offset (the offset relative to the longitudinal axis of the bone plate) and also the slope of the screw axis (relative to a line normal to the plate axis) can be precisely delimited in advance, within an angular range of, say, ±22°, and within defined limits.

By means of the spring mechanism, the geometry of the plate end of the drilling guide can be changed in such a manner that holes for screws can be made in neutral as well as offset position, in order to achieve no compression effect or a quantitatively pre-determined compression effect, as desired.

Moreover, thanks to the projecting plate end segment of the hollow cylinder that acts as a drill bushing, the drill guide can also be used as guide sleeve. For this purpose the internal cylinder may be built in various lengths.

Since the distal or plate end of the drill guide according to the invention has a shape identical with the shape of the underside of the head of the screw to be implanted, a set of drill guides in graduated sizes to accord with the various screw sizes should be maintained.

One embodiment of the invention, which explains its operating principle, is illustrated in the drawings and is described below in greater detail.

BRIEF DESCRIPTION OF THE DRAWINGS

In the drawings:

FIG. 2 is a schematic view partly in longitudinal section, of a drill guide according to the invention, positioned with spring mechanism loaded, in a compression hole of a bone plate;

FIG. 3 is a schematic view partly in vertical section of a drill guide positioned in a compression hole of a bone plate without loading of the spring mechanism;

FIG. 4 is a schematic view partly in vertical section of a drill guide according to the invention positioned in a compression hole of a bone plate without loading the spring mechanism.

FIG. 5 is a schematic view partly in vertical section of a plate/screw combination illustrating the result achieved through the use of a drill guide positioning according to FIG. 4;

FIG. 8 is a schematic view, partly in vertical section of a drill guide according to the invention, positioned for drilling at an oblique angle to the longitudinal axis of a plate;

FIG. 9 is a schematic view partly in vertical section through the plate-screw combination according to FIG. 8.

DETAILED DESCRIPTION OF THE INVENTION

Figure 1:
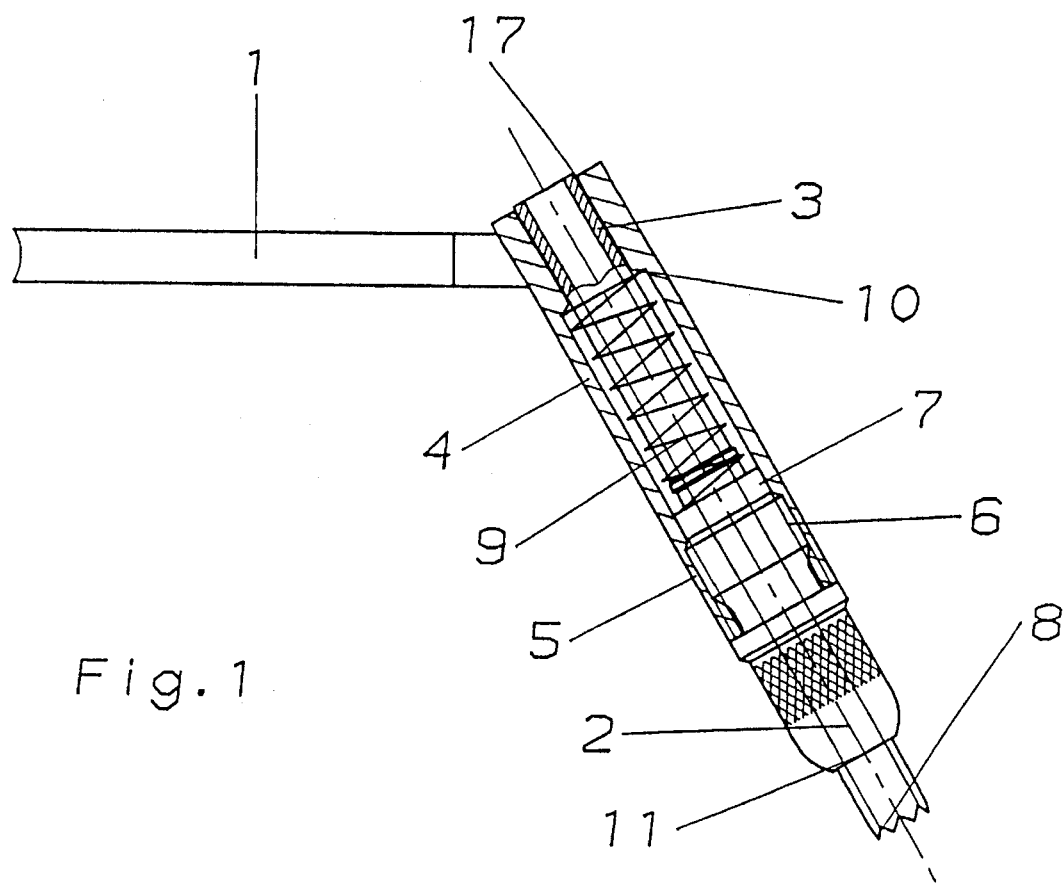
FIG. 1 is a view partly in side elevation and partly in vertical section of a drill guide according to the invention.

The drill guide illustrated in FIG. 1 consists of an external hollow cylinder 4 that has a support arm 1 and in which an internal hollow cylinder 3 is positioned so that it can be slid axially. The axial sliding capability of the internal hollow cylinder 3 is limited on the one hand by a retainer 2, and on the other hand by a spring 9 which tends to force the inner cylinder 3 toward the distal, or plate, end of the outer cylinder 4.

By means of a proximally positioned external thread 6, the retainer 2 can be screwed into a corresponding distally positioned internal thread 5 of the external hollow cylinder 4. The terminal exterior shape of the retainer 2 corresponds as identically as possible to the spherical profile of the underside of the head of the round-headed screw to be used. Thus with the retainer 2 inserted, the distal end of outer cylinder 4 has a shape identical to the shape of the underside of the screw to be inserted. With the retainer 2 in screwed-in position and ready for use, as illustrated in FIG. 1, the distal end segment 8 of inner hollow cylinder 3, which end segment has a serrated edge 8a, extends through the distal opening 11 of retainer 2. Its exterior shape corresponds to the shank profile of the bone screws to be used (cf. FIGS. 4 and 5). Overall, then, the exterior shape of the distal segment 2, 8 of the drill guide corresponds to the exterior contour of the bone screws to be used.

The spiral spring 9 is fixed between a radial stop 7 on the inner hollow cylinder 3 and a shoulder 10 of the outer hollow cylinder 4. When under stress, e.g. when spring 9 is compressed, the rear proximal segment of the inner hollow cylinder 3 projects outward through the proximal opening 17 of the outer hollow cylinder 4. This is illustrated in FIG. 2.

The exterior geometry of the distal or plate end of the drill guide is such that when the drill guide is inserted into the drill hole 12 of a bone plate 13, the bone screw 14 to be positioned, as illustrated in FIG. 3, moves into a neutral position in which no compression effect is exerted when the screw 14 is inserted. The surgeon can control this procedure visually by observing the proximal segment of the inner hollow cylinder 3, which projects out of the drill guide.

This proximal segment of the inner hollow cylinder 3 may have optical markings 3a, for example colored rings, which make it possible to graduate the degree of extension of the drill guide so that various degrees of compression can be achieved.

On the other hand, if no pressure is exerted on the drill guide (and hence on edge 8a of inner hollow cylinder 3), spring 9 can relax, so that the distal or plate end segment 8 of the inner hollow cylinder 3 projects a certain distance out of the retainer 2. By means of the projection of the distal end segment 8 of the inner hollow cylinder 3 from the inside of the retainer 2, the plate side exterior contour of the drill guide changes so that (as illustrated in FIGS. 4 and 5) it is slid longitudinally opposite the neutral position in compression hole 12 of bone plate 13 by a pre-determined amount (in this case 1.0 mm), leading to a compression effect of the screw 14 to be inserted. The surgeon can control this procedure visually by observing the proximal segment, with the inner hollow cylinder 3 being in this case flush with the outer hollow cylinder 4.

Figure 6:
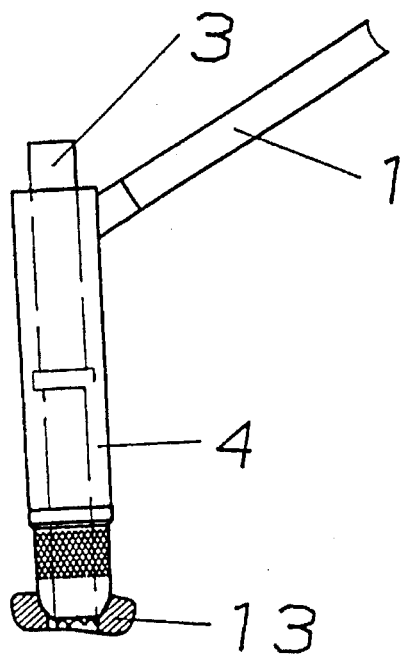
FIG. 6 is a schematic view partly in vertical section of a drill guide according to the invention performing an oblique-angled drilling.

The use of a drill guide according to the invention to perform oblique-angled drilling is illustrated in FIG. 6. The screw 14 illustrated in FIG. 7, which is inserted by use of the drill guide positioning illustrated in FIG. 6, has a screw axis 18a inclined by an angle of 60 /2 to the axial plane of symmetry 18 of the bone plate 13.

FIG. 8 shows the position of the drill guide when drilling is made at an oblique angle to the longitudinal axis of the plate.

Figure 7:
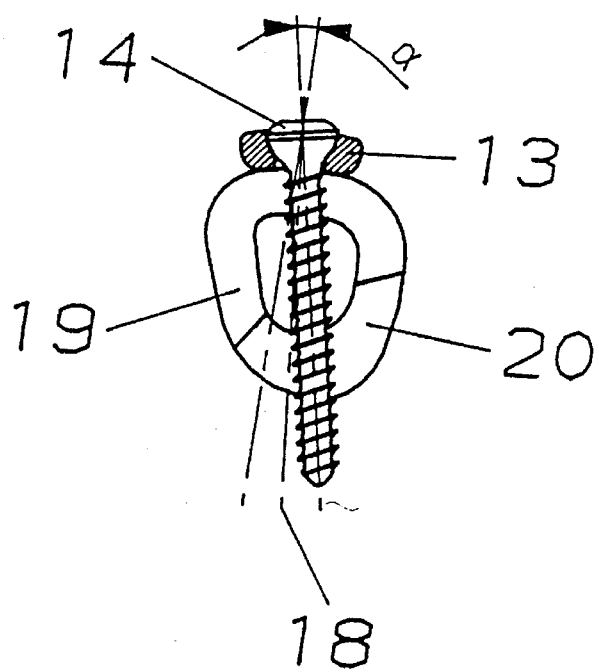
FIG. 7 is a view in vertical section through a plate-screw device mounted in the bone using the drill guide positioning according to FIG. 6.

FIG. 9 shows the screw 14, shown also in FIG. 7, in the middle plane (plane of axial symmetry) of the bone plate running through the longitudinal axis of the plate, and the hollow bone with bone fragments 19 and 20 being held together by the screw 14. In this plane, screw 14 forms an angle of $\beta/2$ in the orthogonal plane passing through the longitudinal axis of the plate.

Combined angle positions of the screw 14 sideways and longitudinally are possible within the indicated angle ranges of $\alpha$ and $\beta$. However, thanks to its exterior geometry, the drill guide limits drilling within the pre-determined inclination ranges which increases security.

Figure 10:
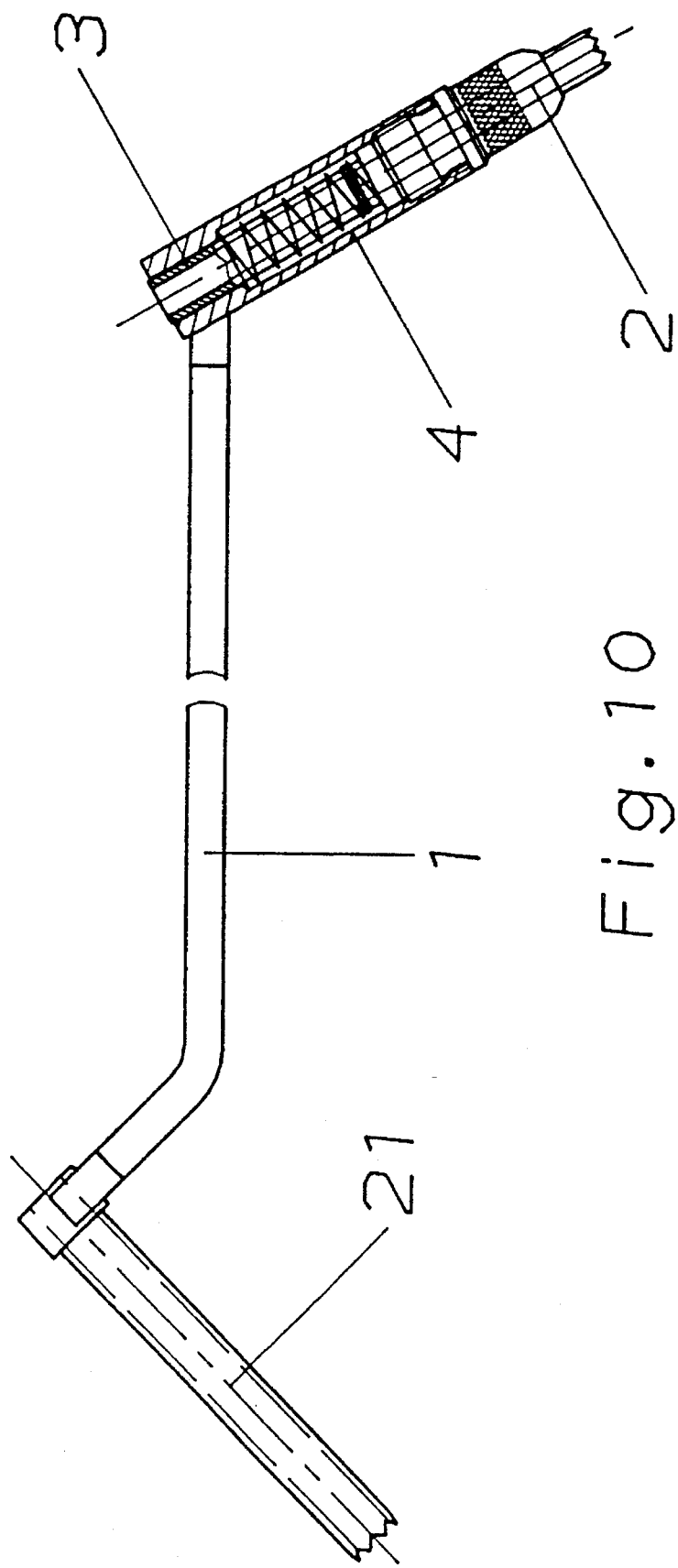
FIG. 10 is a schematic view, partly in vertical section of a drill guide according to the invention with an additional drill bushing positioned on the support arm.

In a preferred embodiment of the drill guide according to the invention, as illustrated in FIG. 10, an additional drill bushing 21 having an internal diameter that is larger than the inner hollow cylinder 3 is positioned on the supporting arm 1. Thus, for example, if the internal diameter of the inner hollow cylinder 3 is 3.2 mm (this should correspond to the diameter of the tap drill to be used in the individual case), the internal diameter of the additional drill bushing 21 would be 4.5 mm. This makes is possible to enlarge drill holes of 3.2 mm diameter in the proximal area of the adjacent cortex, in order to permit applications of bone screws with a proximal smooth, large shank.

A principal advantage of a drill guide according to the invention is that the drill guide segments that engage with plate hole 12 accord exactly with the under surface 15 of the screw head and the exterior diameter of the screw threading. This means that in contrast to the situation with conventional drill guides, a geometrically correct adjustment can be achieved in any desired position. Another advantage is that the hemispherical bottom of the drill guide that engages with plate hole 12 is extended cylindrically by the projection of the inner hollow cylinder 3, so that no screw positioning that creates side slippage can be carried out when the screw is temporarily screwed through the edge of the plate hole 12. Lateral forces constitute an additional load on the bone, and can lead to a situation in which the torsional moments thereby occurring slide the previously adjusted bone fragments such as 19, 20 toward each other or in which intact bone segments are subjected to parasitic tensions.

Another advantage of the drill guide according to the invention is that with the telescoping distal end segment of the inner hollow cylinder 3 gradually varying compressions can be achieved with any desired inclination of screw 14. Another definite advantage is the fact that the telescoping structure and its geometric embodiment with a hemisphere shape makes it possible to exert compression without any need to change the drill guide, as is necessary with conventional drill guides. A final advantage is to be seen in the fact that a drill guide according to the invention can be used as a plug-in drill bushing so as to orient the plate position precisely to the screw position and guarantee a precise and stress-free osteosynthesis.

What is claimed is:

1. Drill guide for drilling screw holes in fractured bone segments comprising a rigid, incompressible, integrally formed hollow outer cylinder having a longitudinal axis, a handle extending outwardly from said outer cylinder, a hollow inner cylinder having a length greater than the length of said outer cylinder, slidingly positioned coaxially within said outer cylinder, and a spring mechanism in said outer cylinder acting upon said inner cylinder to extend the distal end of said inner cylinder beyond the distal end of said outer cylinder, said inner and outer cylinders being arranged to receive coaxially and guide a drill bit while leaving said drill bit free for rotational and axial movement.

2. Drill guide for drilling screw holes in bone fragments to be stabilized by means of a compression bone plate having screw holes and of round headed screws adapted to fit said screw holes, said guide comprising an inner hollow cylinder having a drill side end and a plate side end, an outer hollow cylinder having a drill side end and a plate side end and a spring mechanism within said outer cylinder, said inner cylinder being of greater length than said outer cylinder and positioned in said outer cylinder in a manner such that it can be slid axially by said spring mechanism and by a compressive force applied to its plate side end, said inner cylinder being arranged to guide a drill bit while leaving said drill bit free to rotate and move axially, the plate side end of the outer cylinder having the shape of the head of the screw to be inserted and the inner cylinder having a diameter which is the same as the diameter of the shank of the screw to be inserted.

3. Drill guide according to claim 2, wherein the plate side end of the inner cylinder, which extends beyond the outer cylinder, is of a size such that, when the spring is uncompressed, a hole may be created that is displaced longitudinally for a specific distance toward a neutral position in the screw hole of the compression plate.

4. Drill guide according to claim 2, wherein the drill side end of the inner cylinder has optical marking.

5. Drill guide for drilling plate screw holes in bone fragments to be stabilized by means including a compression bone plate having screw holes and round-headed screws, said guide comprising an inner hollow cylinder positioned in such manner that it can be slid axially by means of a spring mechanism which inner hollow cylinder is positioned in an outer hollow cylinder and is designed to guide a drill, the plate-side end of the outer hollow cylinder and the plate-side end of the inner hollow cylinder, which latter plate-side end projects beyond the plate side end of the outer cylinder, having, respectively, the identical spherical shape of the underside of the screw head and the shank of the screw to be inserted, said drill guide further comprising a support arm and an additional drill bushing on the support arm, said additional drill bushing having a larger internal diameter than the inner hollow cylinder for use as a tissue protection sleeve.

* * * * *

UNITED STATES PATENT AND TRADEMARK OFFICE
CERTIFICATE OF CORRECTION

PATENT NO. : 5,507,801
DATED : April 16, 1996
INVENTOR(S) : Paul Gisin and Stephan M. Perren It is certified that error appears in the above-identified patent and that said Letters Patent is hereby corrected as shown below:

Col. 3, line 55, delete "60/2" and insert --$\alpha/2$--.

Signed and Sealed this

Tenth Day of February, 1998

Attest:

BRUCE LEHMAN

Attesting Officer          Commissioner of Patents and Trademarks